(12) United States Patent
Felix

(10) Patent No.: US 8,474,679 B2
(45) Date of Patent: Jul. 2, 2013

(54) INSTRUMENT FOR APPLYING A SURGICAL FASTENER

(75) Inventor: Augustus Felix, Cranston, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 17 days.

(21) Appl. No.: 12/501,831

(22) Filed: Jul. 13, 2009

(65) Prior Publication Data

US 2011/0006104 A1    Jan. 13, 2011

(51) Int. Cl.
*A61B 17/064* (2006.01)

(52) U.S. Cl.
USPC .................. 227/179.1; 227/175.1; 227/19

(58) Field of Classification Search
USPC ............... 227/175.1, 179.1, 19; 606/139
See application file for complete search history.

(56) References Cited

U.S. PATENT DOCUMENTS

| | | | | |
|---|---|---|---|---|
| 5,607,095 | A * | 3/1997 | Smith et al. ................ | 227/177.1 |
| 6,773,438 | B1 * | 8/2004 | Knodel et al. ................ | 606/139 |
| 7,229,452 | B2 * | 6/2007 | Kayan ........................... | 606/142 |
| 7,758,612 | B2 * | 7/2010 | Shipp ............................ | 606/219 |
| 2007/0088390 | A1 * | 4/2007 | Paz et al. ...................... | 606/232 |
| 2008/0243143 | A1 * | 10/2008 | Kuhns et al. ................. | 606/139 |

OTHER PUBLICATIONS

International Search Report and Written Opinion from PCT/US10/01948 mailed Sep. 1, 2010.

* cited by examiner

*Primary Examiner* — M. Alexandra Elve
*Assistant Examiner* — Andrew M Tecco
(74) *Attorney, Agent, or Firm* — Wolf, Greenfield & Sacks, P.C.

(57) ABSTRACT

An instrument for applying one or more surgical fasteners includes a tubular shaft having a distal end through which each fastener is deployed. A delivery system is contained within the tubular shaft for advancing the surgical fasteners along, and out of, the instrument. An actuator is operatively associated with the delivery system. One or more wall structure modifications in the tubular shaft, such as openings, reliefs or cut-outs, interact with the delivery system. An outer tubular shaft is mounted over the wall structure modifications to reinforce the instrument against permanent deformation or inward distortion if excessive forces are encountered.

7 Claims, 4 Drawing Sheets

INSTRUMENT FOR APPLYING A SURGICAL FASTENER

FIELD OF INVENTION

The invention relates to an instrument for applying a surgical fastener.

BACKGROUND

Surgical fasteners are widely used in many different procedures. For example, staples, sutures, clips and other fasteners are commonly used in laparoscopic and open surgical procedures to secure together two or more portions of approximated tissue, or to attach a prosthetic repair fabric, such as surgical mesh fabric, to tissue surrounding a defect as in a hernia repair operation.

Instruments for applying surgical fasteners typically include an elongated shaft that extends away from a handle end. A slender shaft profile may be desired to provide handleability and ease of use, as well as to ensure compatibility with the 5 mm and smaller trocars used in various laparoscopic procedures. Another design criteria is to increase the space within the shaft that accommodates the internal workings of the instrument, such as the surgical fastener delivery system, but without enlarging the overall shaft profile. A common approach for achieving both of these objectives is to reduce the wall thickness of the shaft; the outer profile is unchanged while the inner diameter of the shaft is increased.

To manipulate tissue or to otherwise effect the surgical site, the physician may lever or angle the thin walled, elongated instrument and, at times, may apply considerable force from the handle end to the remotely located distal end. Should excessive levels of force be applied, there may be a potential for the thin walled shaft to permanently bend or otherwise deform, or at least to deflect inwardly so as to interfere with the internal components of the instrument, such as the surgical fastener deliver system. Certain surgical fastener delivery instruments include cut-outs, reliefs, or other modifications in the wall structure of the elongated shaft, and the inventors have discovered that these wall structure modifications may be susceptible to a permanent bend or inward distortion in response to excessive forces applied to the instrument, particularly if the instrument is being levered or angled against a trocar through which the instrument has been inserted to reach the surgical site.

SUMMARY

In one aspect of the invention, an instrument for applying a surgical fastener is provided that includes an inner tubular shaft having a proximal end and a distal end. A delivery system is contained within the inner tubular shaft for advancing at least one surgical fastener out of the distal end. An actuator is operatively associated with the delivery system. An outer tubular shaft is mounted about, and reinforces, the inner tubular shaft.

In another aspect of the invention, an instrument for applying a surgical fastener is provided that includes a tubular shaft having a proximal end and a distal end. A delivery system is contained within the tubular shaft for advancing at least one surgical fastener out of the distal end. An actuator is operatively associated with the delivery system. A predetermined portion of the tubular shaft is susceptible to inward distortion or permanent deformation if excessive force is applied to the instrument, and such predetermined portion is reinforced.

In a still further aspect of the invention, a method of manufacturing an instrument for applying a surgical fastener is provided. An instrument includes a tubular shaft having a distal end. A delivery system is contained within the tubular shaft for advancing at least one surgical fastener out of the distal end. An actuator is operatively associated with the delivery system. A predetermined portion of the tubular shaft is susceptible to inward distortion or permanent deformation if excessive force is applied to the instrument. During manufacture, the predetermined portion of the tubular shaft is reinforced.

These and other aspects of the invention will be apparent from the following description and claims.

BRIEF DESCRIPTION OF THE DRAWINGS

Other aspects, advantages and novel features will become more apparent from the following detailed description of embodiments of the invention when considered in conjunction with the accompanying drawings wherein.

DETAILED DESCRIPTION OF EMBODIMENTS

Figure 1:
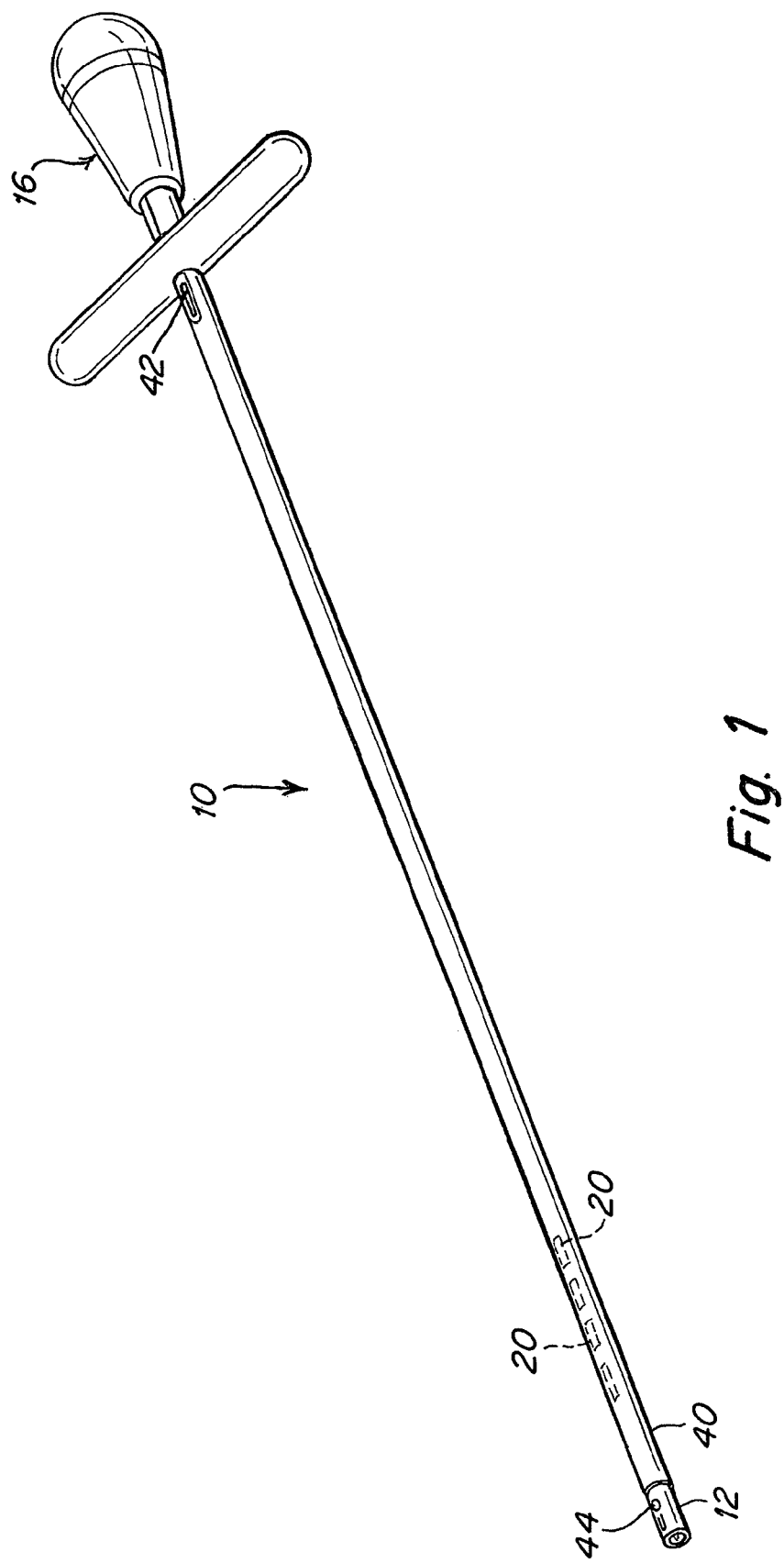
FIG. 1 is an illustration, partially in phantom, of an instrument for applying a surgical fastener.
Figure 2:
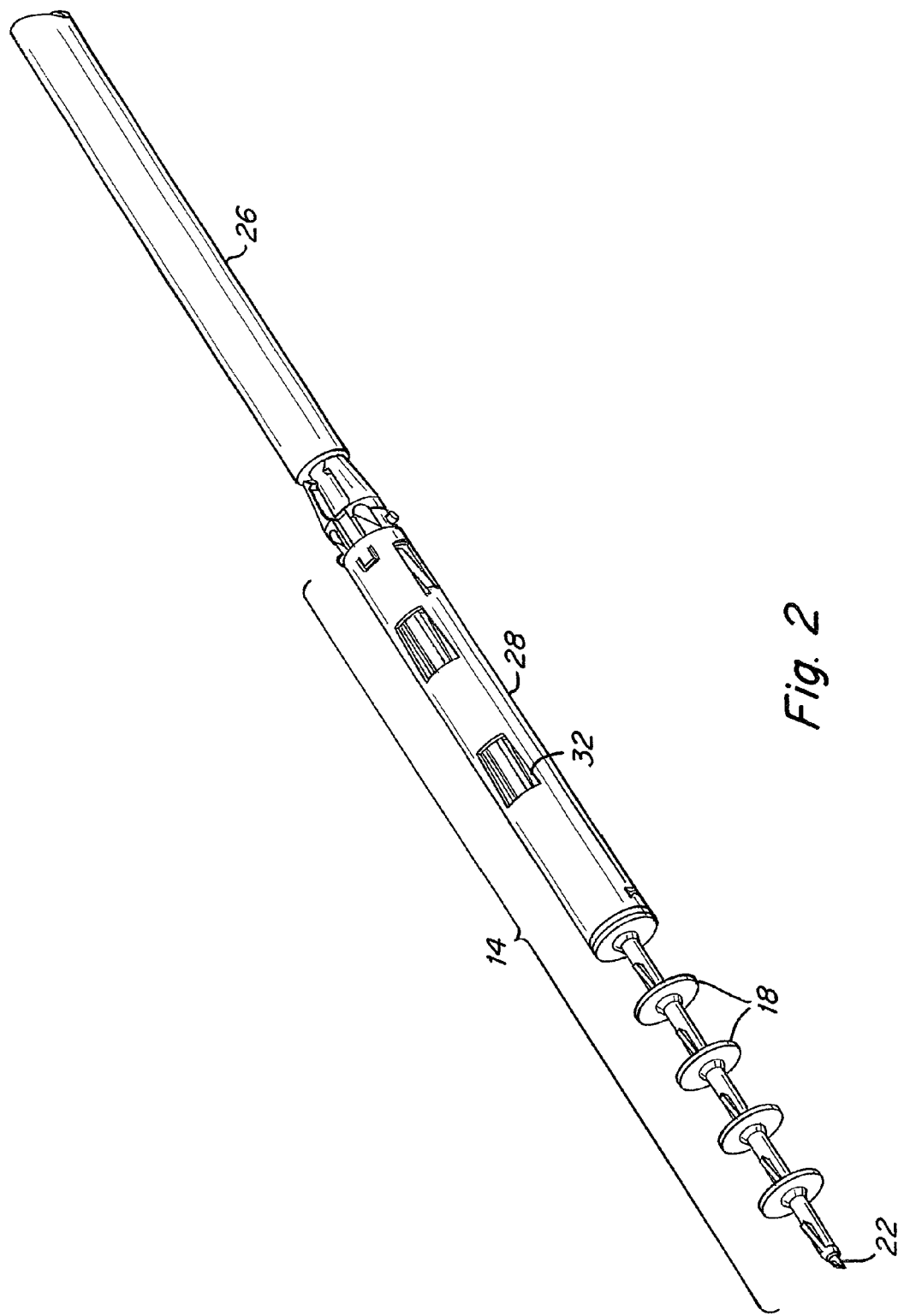
FIG. 2 is an illustration of an instrument for applying a surgical fastener with the reinforced tubular shaft removed, revealing the surgical fastener delivery system.
Figure 3:
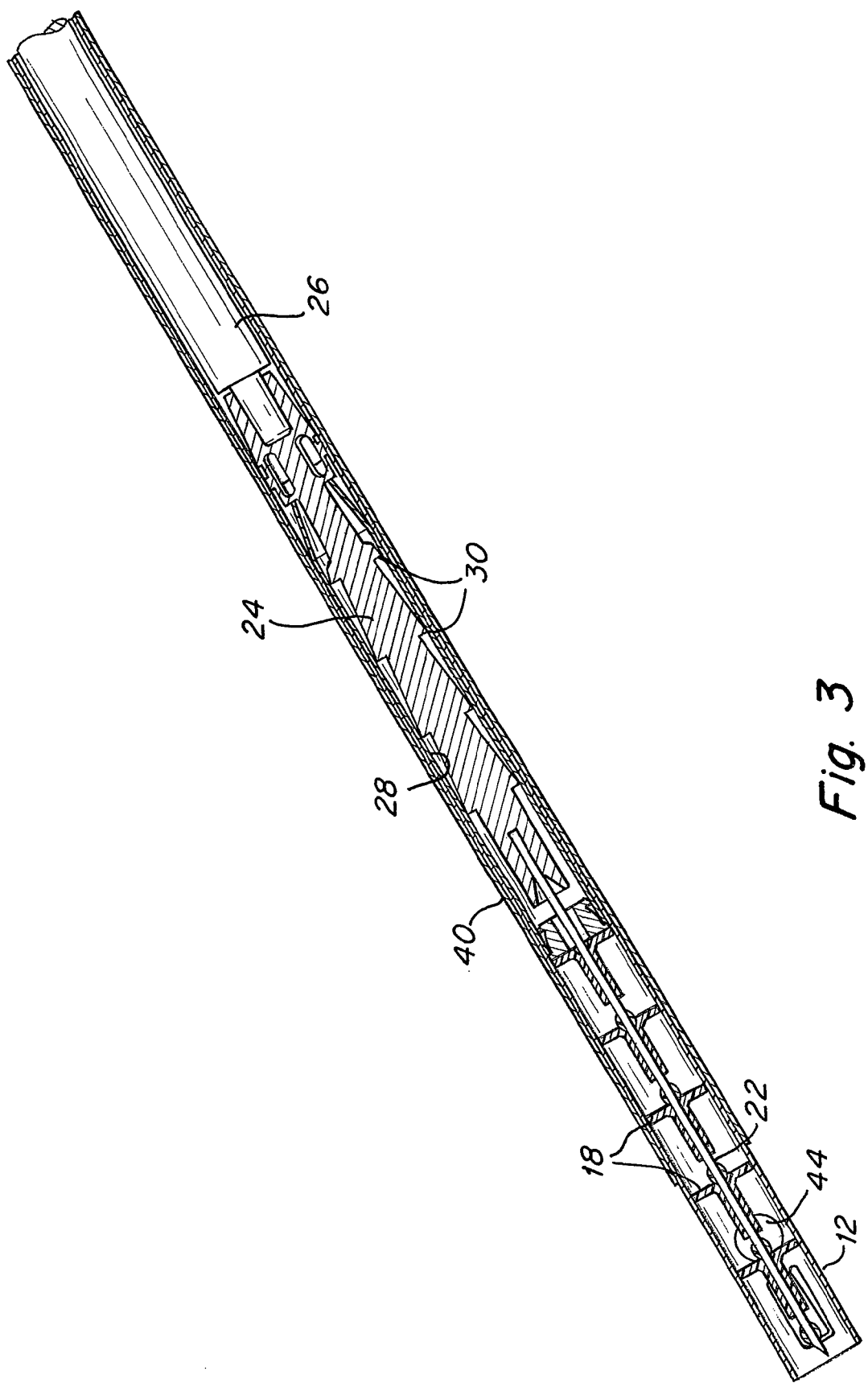
FIG. 3 is a sectional view of the instrument of FIG. 2 (including the reinforced tubular shaft)
Figure 4:
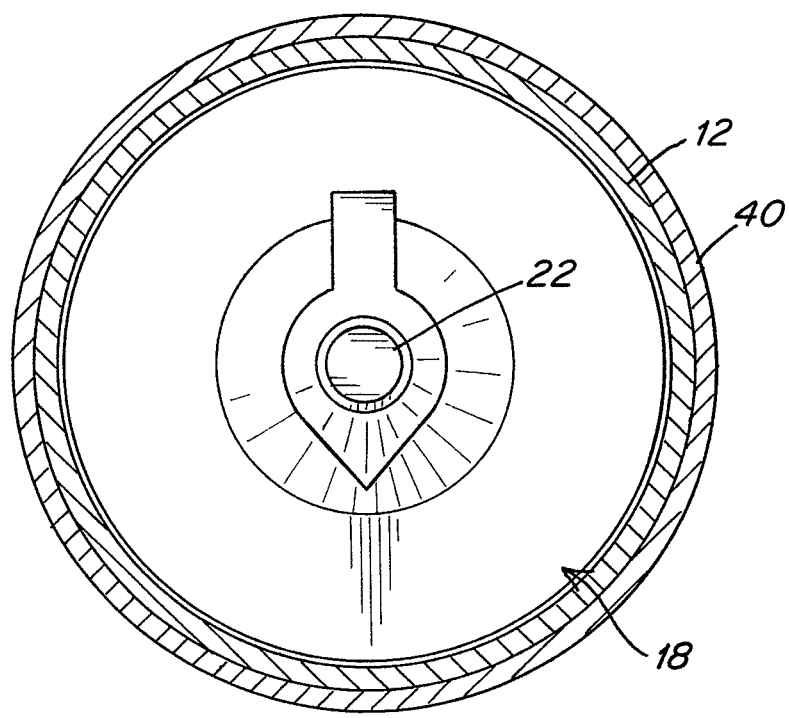
FIG. 4 is an end view of an instrument, handle removed, for applying a surgical fastener, showing an outer tubular shaft reinforcing an inner tubular shaft.

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

As shown in the Figures, an instrument 10 for delivering at least one surgical fastener may include an elongated tubular shaft 12 having a proximal end adjacent a handle and a distal end with an exit opening for release of the surgical fastener. A delivery system 14 is contained within the tubular shaft and, in response to an actuator 16 manipulated by a physician, advances the surgical fastener out of the instrument into the target site. The instrument may be preloaded with a stack of surgical fasteners 18, and the delivery system may be configured to advance the stack of surgical fasteners down the elongated shaft and out of the exit opening one fastener at a time. The instrument may be sized and dimensioned for laparoscopic procedures, that is for insertion through a trocar (such as a 5 mm trocar or other sizes, both larger and smaller), or for use in an open surgical procedure.

The tubular shaft may be formed of metal, such as stainless steel, and may be thin walled. The tubular shaft may have a wall structure modification including, without limitation, one or more openings, cut-outs and/or reliefs. The wall structure modification may assist in the delivery of the surgical fastener, enhance the handle-ability of the instrument, reduce the weight of the device, facilitate sterilization, and/or provide other attributes. In the particular embodiment shown in the Figures, the wall structure modification includes a series of tab shaped, diametrically opposed, axially spaced, cut-outs 20 (shown in phantom in FIG. 1) that cooperate with the delivery system contained within the tubular shaft.

A stack of surgical fasteners are loaded onto a needle 22 that is contained within the distal region of the shaft. The needle extends from a ratchet coupling 24 that, in turn, extends from an actuator rod 26. A pusher sleeve 28 is mounted over the ratchet coupling, and is in end-to-end contact with the stack of surgical fasteners. The needle extends through the pusher sleeve. A series of barbs 30 are located on the ratchet coupling and have a ramp or wedge shape, tapering from a larger distal end to a narrower proximal end. The pusher sleeve is moveable over the barbs in a distal direction but is prevented by the larger end of the barbs from moving in a proximal direction. Depression of the actuator distally shifts the actuator rod and ratchet coupling. The pusher sleeve, in contact with a barb end, is similarly moved in the distal direction. A cooperating relief or opening 32 on the pusher sleeve engages with one of the tab cut-outs on the shaft, holding the pusher sleeve in the advanced position. As the actuator rod returns at the end of the stroke, the ratchet coupling is drawn proximally as well. Due to the tapering shape of the barbs, the ratchet couple slides relative to the pusher sleeve that is held by the shaft. The next barb on the ratchet coupling engages with the tab cut-out on the pusher sleeve, so that the pusher sleeve has moved one barb length, also corresponding to a surgical fastener length, relative to the ratchet coupling. The pusher sleeve remains in contact with the ratchet coupling and the device is ready to deploy the next fastener. In this fashion, the stack of fasteners is controllably advanceable down the shaft one surgical fastener length at a time, with each stroke corresponding to the deployment of an individual surgical fastener.

An outer tubular shaft 40 is mounted over the inner tubular shaft, reinforcing the instrument at the location of the wall structure modifications. The outer tubular shaft may be joined to the inner tubular shaft; for example, and without limitation, the outer tubular shaft may be laser welded to the inner tubular shaft at one or more locations. In a representative arrangement, a circumferential laser weld is formed near the distal and proximal ends of the outer tubular shaft. With this particular assembly, the inner tubular shaft and outer tubular shaft are fixedly positioned relative to each other. Laser welding or other technique for uniting the outer and inner shafts may take place prior to loading of the instrument with one or more surgical fasteners, to avoid compromise of the surgical fastener, but also may proceed after the fasteners have been installed in the instrument.

The outer tubular shaft may be formed of metal and may be formed of the same or a different material as the inner tubular shaft. The outer tubular shaft may be thin walled and have the same, or a different, wall thickness as the inner tubular shaft. Portions of the outer tubular shaft may include openings or reliefs. For example, as shown in FIG. 1, a stop pin 42 may extend through a slot in the inner tubular shaft that limits the stroke of the actuator. The outer tubular shaft may be configured to accommodate the stop pin. Similarly, one or more windows 44 at the end of the inner tubular shaft may be provided to indicate when the last surgical fastener is ready for deployment. The outer tubular shaft may end before the windows or include openings to allow visualization of the windows in the underlying shaft. Although shown as substantially continuous in surface, except for the opening for the stop pin, the outer tubular shaft may have a more open or porous structure. For example, and without limitation, the outer tubular shaft may be in the form of a lattice or other open, exoskeleton type arrangement. The illustrated outer tubular shaft is cylindrical, but the invention is not limited to a particular shape and other configurations may be employed as should be apparent to one of skill in the art.

The outer tubular shaft may be constructed and arranged to increase the resistance of the instrument to permanent deformation due to externally applied forces by a select amount. For example, and without limitation, resistance to permanent deformation may be increased by at least 50% as compared to an unreinforced instrument and, more preferably, by at least 100%. Although an over-shaft arrangement has just been described, other approaches are contemplated for reinforcing the tubular shaft containing the surgical fastener delivery system, as should be apparent to one of skill in the art. For example, and without limitation, the composition of the tubular shaft relative to the structural wall modifications may be selected to resist buckling or distortion, or localized portions of the inner tubular shaft, where the structural wall has been modified, if not the entire length of the shaft, could be subject to special processing, such as heat treatment, to enhance wall strength.

The instrument is not limited to a particular type of surgical fastener. The fastener may be a tack, a screw, an o-ring, a q-ring, a clip, a helical wire coil, or other fixation device suitable for securing two or more portions of soft or hard tissue together or for attaching a surgical repair fabric, such as a mesh, or other prosthetic device or implantable object to soft or hard tissue. The surgical fastener may be absorbable or non-absorbable, and may be formed from a variety of materials including synthetic and natural polymers, metals, combinations of any of the foregoing, or any other material or combination of materials. A suitable surgical fastener is a PERMASORB® absorbable [Poly (D, L)-lactide (PDLLA)] tack available from Davol, Inc.

The instrument may be configured to hold and deliver one or more surgical fasteners, with representative arrangements including devices arranged to deploy a five (5) or twelve (12) count of surgical fasteners which may be preloaded in the instrument. The instrument may deploy a surgical fastener using a manually operated mechanism, a motorized mechanism, or a combination of manual and motorized mechanism. The just described surgical fastener delivery system is a manually operated system that is particularly suited for applying a PERMASORB® tack. However, the instrument is not limited to a particular surgical fastener delivery system, and other deployment systems are contemplated as appropriate for the surgical fastener of interest. Thus, the delivery system may include, for example and without limitation, a rotator and associated thread form that advances one or more fasteners towards the distal end of the instrument and discharges each fastener into the tissue, prosthetic fabric, or other area of interest. Such a rotator may be arranged to engage the interior of a fastener (i.e., through-bore) or an exterior of the fastener, with the thread form engaging the other surface. Alternatively, the instrument may be provided with a plunger type system for driving the fastener out of the instrument with a thread form at a distal end of the shaft causing the fastener to wind its way into the tissue, prosthetic repair fabric, etc., as it exits the applicator. Again, the instrument is not limited to a particular arrangement for moving a surgical fastener down the instrument or for deploying the surgical fastener out of the instrument. The instrument may include, but does not require, a needle or other structure for penetrating or piercing the delivery site, prior to or during deployment of the surgical fastener.

A representative instrument includes a single use, disposable tack applier having a thin-walled (0.007 inches), stainless steel, inner tubular shaft with a length of 37-38.5 cm for laparoscopic applications and 17-18.5 cm for open procedures. A number of axially extending, tab cut-outs (such as four or five) are formed in opposite walls of the inner tubular shaft. An outer tubular shaft, also thin-walled (0.003-0.006 inches) and made of stainless steel, is mounted directly over the inner tubular shaft and covers the tab cut-outs, reinforcing the inner tubular shaft against buckling or inward distortion if excessive force is applied to the instrument during use, particularly at the region of the tab cut-outs. The outer tubular shaft has a length of approximately 16.5 cm (open) and 36.5 cm (laparoscopic), respectively. The outer tubular shaft may have a matte finish and be laser welded to the inner tubular shaft near a handle end and a distal end. The shaft end of the instrument has an outer diameter that ensures compatibility with most 5 mm trocar cannulas. A 0.6 mm needle is located within the inner tubular shaft and has mounted thereover a stack of through-bore configured surgical tacks (5 or 12 count). The needle extends from a ratchet coupling which is attached to a metal actuator rod. A t-shaped plastic handle is mounted at the proximal end of the inner tubular shaft, and the actuator rod extends through and beyond the t-shaped handle terminating in a bulbous actuator knob. A coil spring is positioned about the actuator rod between the knob and t-shaped handle, and a limit pin extends from the actuator rod through a slit in the inner tubular shaft and a corresponding cut-out in the outer tubular shaft.

The instrument is pre-loaded with surgical fasteners, is packaged and then Ethylene Oxide (ETO) sterilized.

EXAMPLES

The following examples are illustrative only and are not intended to limit the scope of the present invention.

The resistance to permanent bending of instruments for applying surgical fasteners with and without an outer tubular shaft were tested. Testing methodology, results and observations appear below.

A support fixture or jig was provided including a base and a pair of opposed upstanding supports each provided with a notch for receiving, respectively, a region adjacent the tip of the instrument and the region just distal of the t-shaped handle. With the limit pin side of a 12 count (but fastener empty) laparoscopic instrument facing down, the sample is placed in the support fixture and a downward force is applied to the center of the as-supported instrument and increased until the shaft permanently bends. Seven (A) and eight (B) samples, respectively, were tested.

|  | Unreinforced A | Reinforced A | Unreinforced B | Reinforced B |
| --- | --- | --- | --- | --- |
| Average Peak Force (lbs) | 12.39 | 28.24 | 12.50 | 24.84 |
| Location of Bend | Tab cut-out closest to handle | End of internal actuator rod | Tab cut-out closest to handle | End of internal actuator rod |

The average peak force required to permanently bend the tested instruments increased by approximately 100%, or more, for devices including the reinforcing overshaft as compared to the unreinforced instruments. The unreinforced instruments bent at a wall structure modification, a tab cut-out, while the outer shaft reinforced instruments deformed about the end of the metal internal actuator rod at the junction with the ratchet coupling. The data demonstrates superior resistance to buckling or inward distortion when an outer tubular shaft is incorporated into the instruments, which should mitigate the likelihood of damage to the instrument or interference with the functioning of the fastener delivery system if excessive forces are applied to the instrument during surgery, such as might occur due to levering of the instrument against a trocar cannula during a laparoscopic procedure or otherwise.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An instrument for applying a surgical fastener, comprising:
   an inner tubular shaft having a proximal end and a distal end;
   a delivery system contained within said inner tubular shaft for advancing at least one surgical fastener out of said distal end; the at least one surgical fastener loaded onto a needle that is contained within the distal end of the inner tubular shaft;
   wherein said inner tubular shaft includes a sidewall with at least one wall structure modification that is operatively associated with said delivery system, wherein said at least one wall structure modification includes a cut-out that is formed completely through said sidewall;
   an actuator operatively associated with said delivery system; and an outer tubular shaft mounted about, and reinforcing, said inner tubular shaft along said at least one wall structure modification, and
   wherein said inner tubular shaft and said outer tubular shaft are fixedly positioned relative to each other along said at least one wall structure modification.

2. The instrument recited in claim 1, wherein said instrument can resist at least 50% greater peak force before permanently deforming as compared to said instrument without said outer tubular shaft.

3. The instrument recited in claim 1, wherein said instrument can resist at least 100% greater peak force before permanently deforming as compared to said instrument without said outer tubular shaft.

4. The instrument recited in claim 1, further including at least one surgical fastener contained within said inner tubular shaft.

5. The instrument recited in claim 1, wherein said inner tubular shaft and said outer tubular shaft are thin walled and formed of metal.

6. The instrument recited in claim 1, wherein said outer tubular shaft is sized so that said instrument is compatible with a 5 mm trocar.

7. The instrument recited in claim 1, wherein said delivery system includes a ratchet coupling, a pusher sleeve operatively associated with said ratchet coupling and said inner tubular shaft, and a needle extending from said ratchet coupling and through said pusher sleeve.

* * * * *